US00PP10932P

United States Patent [19]

Evison et al.

[11] Patent Number: Plant 10,932

[45] Date of Patent: Jun. 1, 1999

[54] CLEMATIS PLANT NAMED 'EVISTA'

[75] Inventors: Raymond J. Evison, Guernsey, United Kingdom; Mogens N. Olesen, Fredensborg, Denmark

[73] Assignee: Poulsen Roser International, SARL, Souvans, France

[21] Appl. No.: 08/953,042

[22] Filed: Oct. 17, 1997

[51] Int. Cl.[6] ..... A01H 5/00

[52] U.S. Cl. ..... Plt./54.1

[58] Field of Search ..... Plt./54.1

*Primary Examiner*—Elizabeth Kemmerer

[57] ABSTRACT

A new compact Clemantis cultivar which produces large, full, purple flowers which have a darker purple central bar and yellow flower center. The cultivar is compact, climbing, and clinging and flowers well in spring and late summer. The variety successfully propagates from softwood cuttings and is suitable for ornamental use in outdoor settings in a variety of climatic conditions. This new and distinct variety has shown to be uniform and stable in the resulting generations from propagation.

1 Drawing Sheet

SUMMARY OF THE INVENTION

The present discovery constitutes a new and distinct variety of Clematis which originated from a chance seedling and was discovered in a cultivated area. The two unnamed seedlings (parents unknown) were crossed in 1990 and the resulting seed was planted in a controlled environment. The new variety is named 'Evista'.

The objective of the hybridization of this Clematis variety of commercial glasshouse and nursery culture was to create a new and distinct variety with unique qualities, such as:

1. Round form of very large flowers;
2. Golden yellow center;
3. Spring flowering and recurrent flowering habit; and
4. Compact growth.

These qualities required improvement in Clematis varieties that were in commercial cultivation and the objectives have been substantially achieved in the new variety, as evidenced by the unique combination of characteristics that are present in 'Evista' which distinguish it from all other varieties of which we are aware.

'Evista' was selected by Raymond J. Evison and Mogens N. Olesen in their Clematis development program in Domarie Vineries Les Sauvagees, St. Sampsons, Guernsey, Channel Islands, United Kingdom in 1990.

Asexual reproduction of 'Evista' cuttings was first done by Raymond J. Evison and Mogens N. Olesen in Domarie Vineries Les Sauvagees, St. Sampsons, Guernsey, Channel Islands, United Kingdom in 1990. The initial and subsequent propagations have demonstrated that the characteristics of 'Evista' are true to type and are transmitted from one generation to the next.

BRIEF DESCRIPTION OF THE DRAWING

The accompanying color illustration show as true as is reasonably possible to obtain in color photographs of this type, the typical characteristics of the buds, flowers and leaves of the new variety, with different flowers shown in various stages of maturity. Descriptions included are of variety when blooming in autumn. The flower form, flower colors, flower buds, flower pedicel, floral parts, and the cultivar's foliage are depicted.

DETAILED DESCRIPTION OF THE VARIETY

The following is a detailed description of 'Evista', as observed in its growth throughout the flowering period in glasshouses at Domarie Vineries Les Sauvagees, St. Sampsons, Guernsey, Channel Islands, United Kingdom. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing Clematis variety is 'Evione', a variety recently applied for patent status with an Application Ser. No. 08/627,506. Chart 1 details several physical characteristics of the applicant and the comparison varieties.

CHART 1

| | 'EVISTA' | 'EVIONE' |
|---|---|---|
| Color of Tepal - main upper side | Purple RHS 78B | Purple RHS 76A |
| Color of central bar | Dark Purple RHS 78A | Red Purple RHS 71A |
| Vigor | Average | Moderate |
| Spring flower size | 200 mm | 130–180 mm |
| Leaflet shape | Ovate | Lanceolate |

Parents: Chance seedlings.

Classification:

*Botanical.*—*Clematis l.*

*Commercial.*—Early large-flowered cultivar.

Flower and Flower Bud

Blooming habit: Recurrent.

Flower bud:

*Size.*—30–40 mm in length.

*Bud form.*—Elliptic — Ovoid.

*Bud color.*—Green and Red color edging at ¼ opening.

*Tepals.*—Color is R.H.S. 82A of the Purple Color Group.

*Peduncle.*—Surface: Smooth. Length: 80–100 mm average length. Color: Medium Green with Red coloration. Attitute: Erect.

*Borne.*—Singly.

Flower bloom:

*Size.*—Large. 200 mm. on average. Smaller blooms in autumn.

*Form.*—Upon opening, flat. Completely open flat, with tepals straight.

*Color.*—Upon opening, the upper surface is R.H.S. 82A of the Purple Violet Color Group. Upon opening, the reverse side is R.H.S. 82B of the Violet Purple Color Group. After opening, the upper surface is R.H.S. 78B of the Purple Color Group. After opening, the reverse surface is R.H.S. 78C of the Purple Color Group. The base of the tepals is R.H.S. 76C of the Purple Group. The general tonality from a distance is Purple.

*Variations.*—Tepals have dark Purple R.H.S. 78A central bar.

*Fragrance.*—None.

*Lasting quality on plant and as a cut flower.*—Short — Medium lasting.

Tepals:

*Petalage.*—Single. Average range: 6–8.

*Shape.*—Individual tepal shape is elliptic.

*Cross section.*—Slightly reflexed.

*Undulation of margin.*—Medium.

*Tepal apex.*—Narrowly acute.

*Recurvature of tip.*—Slightly curved.

*Persistence.*—Drop off cleanly.

*Arrangement.*—Tepals are arranged regularly.

Reproductive organs:

*Pollen.*—Color: Cream. Abundance: Average.

*Anthers.*—Size: Medium — Large. Color: Yellow. Arrangement: Regular.

*Filaments.*—Color: White.

*Stigmas.*—Location: Central and protruding. Color: Pinkish yellow.

*Styles.*—Color: Grey/green.

*Ovaries.*—Normal.

Plant

Plant form: Climbing and spreading.

Plant growth: Average vigor.

Height: Seasons growth attains 2–2.5 meters.

Hardiness: Trials to date show the variety hardy in USDA Zones 4–9.

Stems:

*Color.*—Young wood: Red. Older wood: Brown.

*Internodes.*—Cylindrical. Length: 120–170 mm.

*Petioles.*—Incidence: Moderate. Size: Average length: 60–90 mm. Color: Green. Clasping: Clasps by leaf petiole.

*Bark.*—Young wood: Smooth. Older wood: Smooth.

Plant foliage: Deciduous, Trifoliate.

*Leaf size.*—Medium. Length 80 mm.

*Abundance.*—Average.

*Color.*—Top: Medium green. R.H.S. 137B of the Green Color Group. Bottom: Medium green. R.H.S. 137C of the Green Color Group. New growth: Reddish green internodes. Light Green foliage. Older growth: Red internodes. Dark green foliage.

Plant leaves and leaflets:

*Stipules.*—Absent.

*Petiole.*—Length: 60–90 mm. Underneath: Without prickles.

*Leaf edge.*—Terminal leaflet margin is entire.

*Shape.*—Base of leaflet: Rounded. Apex of leaflet: Acute.

*Leaf surface.*—Upper side: Glabrous. Lower side: Ribbed. Matte finish.

Disease resistance: Subject to any disease that normally attacks the species.

We claim:

1. A new and distinct variety of Clematis plant, substantially as herein shown and detailed, as a distinct and novel clematis variety due to its abundant large violet-purple striped flowers with yellow center, good keepability, attractive long lasting foliage and compact growth, suitability for production from softwood cuttings in pots, durable flowers and foliage which make the variety suitable for distribution in the nursery industry.

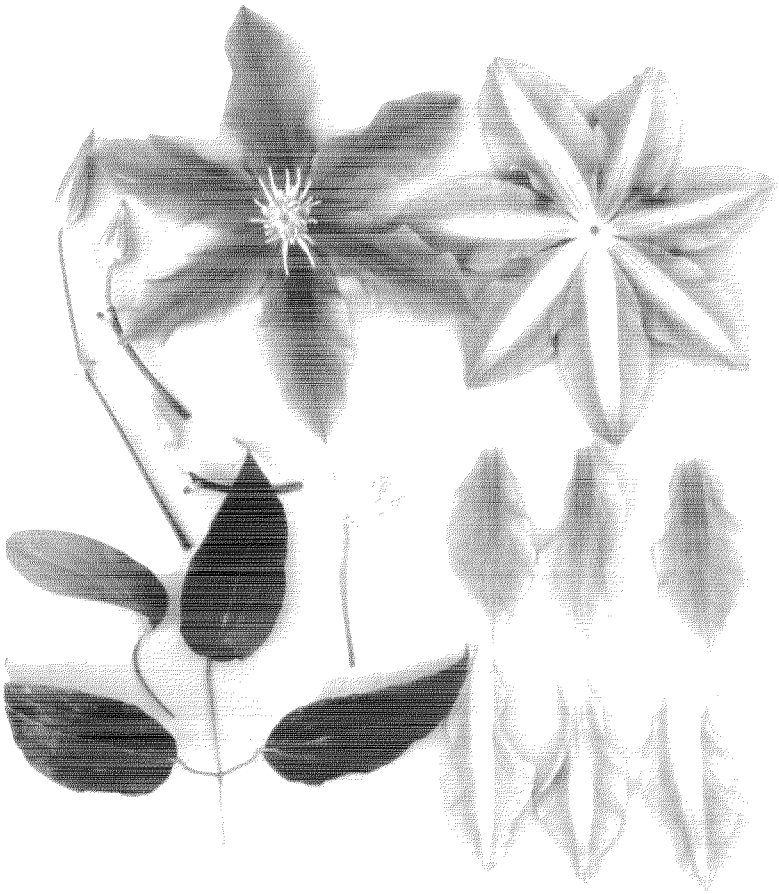

* * * * *